United States Patent [19]

Dimmel

[11] Patent Number: 6,156,155

[45] Date of Patent: *Dec. 5, 2000

[54] METHOD FOR THE DELIGNIFICATION OF LIGNOCELLULOSIC MATERIAL BY ADDING A DIALKYL SUBSTITUTED OCTAHYDROANTHRAQUINONE

[75] Inventor: Donald R. Dimmel, Dunwoody, Ga.

[73] Assignee: Institute of Paper Science and Technology, Inc., Atlanta, Ga.

[*] Notice: This patent issued on a continued prosecution application filed under 37 CFR 1.53(d), and is subject to the twenty year patent term provisions of 35 U.S.C. 154(a)(2).

[21] Appl. No.: 08/994,582

[22] Filed: Dec. 19, 1997

[51] Int. Cl.$^7$ ...................................................... D21C 3/20

[52] U.S. Cl. ............................................. 162/72; 552/269

[58] Field of Search ............................... 162/72; 564/446, 564/447, 458, 459; 552/268, 269, 271

[56] References Cited

U.S. PATENT DOCUMENTS

| | | | |
|---|---|---|---|
| 1,303,168 | 5/1919 | Conover et al. | 552/269 |
| 3,873,580 | 3/1975 | Rennie | 260/362 |
| 4,012,280 | 3/1977 | Holton | 162/72 |
| 4,146,559 | 3/1979 | Bock et al. | 260/563 P |
| 4,826,567 | 5/1989 | Gratzl | 162/72 |
| 5,002,634 | 3/1991 | Dimmel et al. | 162/72 |
| 5,049,236 | 9/1991 | Dimmel et al. | 162/16 |

OTHER PUBLICATIONS

Sarkanen et al., "Lignins–Occurrence, Formation, Structure and Reactions", N.Y., Wiley & Sons, 1971, pp. 43–94.

Butz et al., "Organic Reactions", vol. V; N.Y., Wiley & Sons, 1949, p. 166.

*Primary Examiner*—Steve Alvo
*Attorney, Agent, or Firm*—Fitch, Even, Tabin & Flannery

[57] ABSTRACT

The present invention provides a method for the synthesis of substituted octahydroanthraquinones and substituted anthraquinones which are effective for pulping of lignocellulosics.

4 Claims, No Drawings

METHOD FOR THE DELIGNIFICATION OF LIGNOCELLULOSIC MATERIAL BY ADDING A DIALKYL SUBSTITUTED OCTAHYDROANTHRAQUINONE

This Invention was made with Government support under NREL Subcontract No. XAH-6-15368-01, prime Contract No. DE-AC36-83CH10093 awarded by the Department of Energy. The government has certain rights in this invention.

The present invention relates to a method for producing benzoquinone Diels-Alder adducts effective for pulping of lignocellulosics. More particularly, the present invention provides a method for the synthesis of substituted octahydroanthraquinone and substituted anthraquinone.

BACKGROUND OF THE INVENTION

The wood used in paper making consists essentially of cellulose and hemicellulose fibers bound together by a polymeric material called lignin. A goal of the chemically-based wood pulping processes is to separate the cellulose and hemicellulose from the lignin by degrading the lignin into lower molecular weight species that are soluble in water. In a typical pulping process, wood is added to water that contains sodium carbonate, sodium bicarbonate or sodium hydroxide, and the resulting mixture is heated under pressure to a temperature in the range of 140°–180° C. While the wood lignin may be broken down by reaction with the alkali alone, the process is slow and also results in excessive degradation of the cellulose and hemicellulose which are the desired products. In order to shorten the processing time or lower the processing temperature or both, pulp manufacturers use accelerators such as sodium sulfite or sodium sulfide in the alkali solution to aid in processing.

Sulfur based accelerators reduce the processing time and produce a product superior to that produced by alkali alone, but these additives also introduce additional problems. For example, for the sulfide (kraft) process, malodorous air emissions may occur, and expensive chemical recovery equipment is needed in order to reduce chemical costs. While the sulfur containing systems do present several difficulties to the paper making industry, they are nonetheless the standard process used because they offer the overall greatest flexibility, low chemical costs and strongest paper. For example, the lignin containing spent pulping liquor is burned to produce heat, and the sulfur and caustic are recovered from the furnace and recycled.

An alternative to the use of sulfur accelerators was described by Holton in U.S. Pat. No. 4,012,280 in which the addition and use of quinone compounds such as naphthoquinone, anthraquinone (AQ), phenanthrenequinone, anthrone and their ring substituted derivatives are claimed as accelerators in the wood pulping process. AQ is used at <0.1% levels to improve pulping productivity and lower environmental impacts by (a) increasing pulping rates and product yields, (b) reducing chemical recovery bottlenecks, and (c) providing greater removal of lignin, meaning less organic bleaching by-products. It can be used alone (soda/AQ) or with a kraft process; in the latter case, the sulfur content of the liquor can be reduced and less odorous emissions occur.

While AQ is effective as a catalyst for improving pulping productivity and lowering environmental impacts, the commercial use of AQ is restricted due to its relatively high cost. Even so, kraft/AQ pulping is gaining in popularity, largely because of recent AQ cost reductions and industry's desire to extend production without capital expenditures.

One approach to bringing down the cost of AQ is to prepare a mixture of fused ring quinone type compounds from lignin and lignin derived substances. For example, U.S. Pat. Nos. 5,002,634 and 5,049,236 describe processes whereby lignocellulosics, lignin and lignin derived compounds, such as may be found in black liquor obtained by pulping wood, can be reacted through the use of several oxidation techniques to form a mixture of quinone compounds containing benzoquinones, naphthoquinones, and anthraquinones which can be added to the pulping process to accelerate the lignin degradation process. The economics for the preparation of AQ from lignin is hampered by the overall low yield, typically not more than about 5% yield.

More traditional methods for synthesizing AQ typically involve the reaction of naphthaquinone with 1,3-butadiene to yield tetrahydroanthraquinone. The tetrahydroanthraquinone is further oxidized to form AQ. Other procedures involve oxidation of anthracene and condensation of phthalic anhydride with benzene. However, these synthesis are not well adapted to preparing inexpensive substituted AQ or for allowing easy introduction of substituents into the AQ structure during synthesis.

It is an object of the present invention to provide an efficient method for the synthesis of octahydroanthraquinones and anthraquinones which allows for the introduction of substituents.

It is another object of the invention to provide a method for the delignification of lignocellulosic material using substituted octahydroanthraquinones and substituted anthraquinones as pulping catalysts.

Other objects, advantages, features and characteristics of the present invention will become more apparent upon consideration of the following description and the appended claims.

SUMMARY OF THE INVENTION

The present invention provides a method for the synthesis of high yields of substituted anthraquinones. Substituted anthraquinones are extremely effective as pulping catalysts.

According to the method of the present invention, a benzoquinone is first reacted with a conjugated diene at a time and temperature effective for forming a substituted octahydroanthraquinone in yield of at least about 80%. The substituted octahydroanthraquinone is used directly as a pulping catalyst or can be oxidized under conditions effective for forming a substituted anthraquinone. The method is effective for providing an overall yield of substituted anthraquinone of about 70% or more.

In another aspect, the invention provides a method for delignification of lignocellulosic material. According to the method, substituted octahydroanthraquinone or substituted anthraquinone is added to lignocellulosic material in an amount effective to accelerate and catalyze the delignification of the lignocellulosic material contained therein, the substituted anthraquinone being prepared by the synthesis method of the present invention. The use of substituted anthraquinone in the pulping process results in an increase in pulping efficiency of about twice that of unsubstituted AQ.

DETAILED DESCRIPTION OF THE INVENTION

The method of present invention involves a reaction where a substituted octahydroanthraquinone is formed in a Diels-Alder type reaction. The resulting substituted octahydroanthraquinone can be used directly as a pulping catalyst or can be subsequently oxidized to form a substituted anthraquinone.

As used herein, "anthraquinone" or "AQ" means a compound having the following formula.

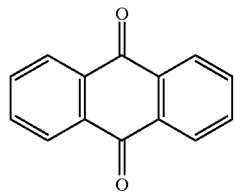

As used herein, a "substituted anthraquinone" means a compound having the general formula

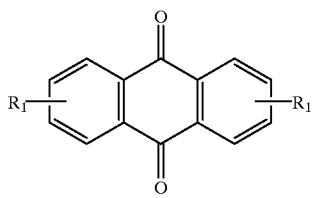

wherein $R_1$ can be the same or different and is selected from the group consisting of $CH_3$ and aliphatic groups having 1 to 8 carbon atoms.

As used herein, "substituted octahydroanthraquinone" means a compound having the general formula

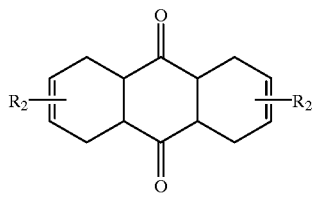

wherein $R_2$ can be the same or different and is selected from the group consisting of $CH_3$ and aliphatic groups having 1 to 8 carbon atoms.

As used herein, a "conjugated diene" means an open chain unsaturated hydrocarbon with double bonds separated by one single bond.

The term "lignocellulosic material" means a wood composition which includes cellulose and hemicellulose fibers bound together with lignin.

Preparation of Substituted Octahydroanthraquinone

In the first step of the synthesis method, about one equivalent of benzoquinone is reacted with about two equivalents of a conjugated diene. In an important aspect of the invention, the benzoquinone is 1,4-benzoquinone or a substituted 1,4-benzoquinone such as 2-methoxy, 2-halo and 2-nitro, and the conjugated diene is 1,3-butadiene or a substituted 1,3-butadiene such as 2-methyl, 2,3 dimethyl, 1-alkyl, 2-alkyl, and 2,3-diethyl. In a very important aspect of the invention, the benzoquinone is 1,4-benzoquinone and the conjugated diene is isoprene (2-methyl-1,3-butadiene).

The benzoquinone and conjugated diene are reacted in an alcohol at about 60° C. to about 180° C. for about 1 hour to about 24 hours. The alcohol utilized in the reaction is selected from the group consisting of ethanol, methanol, propanol, and butanol. In an important aspect of the invention, the reaction of benzoquinone and conjugated diene takes place in ethanol at about 165° C. for about 2 hours.

The reaction of benzoquinone and conjugated diene is effective for providing an isolated yield of substituted octahydroanthraquinone of at least about 80% (based on solvent removal and recrystallization) and at least about 95% GC yield (as determined by addition of an internal standard to the reacted solution). In an important aspect of the invention, the substituted octahydroanthraquinone is 2,6/7-dimethyloctahydroanthraquinone.

Preparation of Substituted Anthraquinone

In another aspect of the invention where substituted anthraquinone is desired, the next step of the synthesis method involves oxidation of the substituted octahydroanthraquinone. In accordance with the method of the invention, the substituted octahydroanthraquinone is oxidized by refluxing the substituted octahydroanthraquinone in alcohol, a base, and oxygen. The alcohol utilized in the reaction is selected from the group consisting of ethanol, methanol, propanol, and butanol, the base is selected from the group consisting of potassium hydroxide, sodium hydroxide, sodium carbonate, and organic bases, and oxygen is supplied with an air stream. The air stream may include compressed air, oxygen, an oxygen enriched air stream or any other oxidant known in the art.

The oxidation of substituted octahydroanthraquinone is effective for providing an isolated yield of substituted anthraquinone of at least about 86%, and an overall isolated yield from benzoquinone and conjugated diene of at least about 70%. In an important aspect of the invention, the oxidation of 2,6/7-dimethyloctahydroanthraquinone results in the production of dimethylanthraquinone (DMAQ).

The following examples illustrate methods for carrying out the invention and should be understood to be illustrative of, but not limiting upon, the scope of the invention which is defined in the appended claims.

Use of Anthraquinone Catalysts in Wood Pulping

The substituted octahydroanthraquinone and substituted anthraquinone of the present invention can be utilized in a number of pulping systems such as soda, kraft and others. In an important aspect of the invention, from about 0.01% to about 0.50% substituted octahydroanthraquinone, based on the weight of the lignocellulosic material, is added to lignocellulosic material to provide a pulping efficiency of at least about 10% higher than the pulping efficiency achieved in a non-catalytic process (i.e. a process where no anthraquinone catalyst is added). The effectiveness of the substituted octahydroanthraquinone may vary as a function of the type of pulping system. For example, the use of substituted octahydroanthraquinone results in about 50% improvement for soda pulping, about 20% improvement for kraft pulping to high kappa numbers, and about a 10% improvement for kraft pulping to low kappa numbers.

EXAMPLES

Example 1: Synthesis of 2,6/7-Dimethyloctahydro AQ and DMAQ

The synthesis of 2,6/7-Dimethyloctahydro AQ and DMAQ is conducted according to the following reactions.

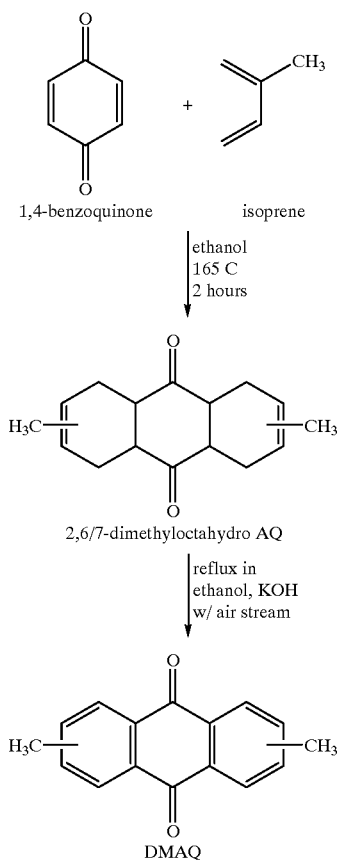

1,4-benzoquinone    isoprene ethanol
165 C
2 hours 2,6/7-dimethyloctahydro AQ reflux in
ethanol, KOH
w/ air stream

DMAQ

Diels-Alder Reactions Between Benzoquinone and Isoprene to give the Bis-Adduct

A mixture of benzoquinone (1.0 mole) and isoprene (2.0 mole) in ethanol (300 mL) was sealed in a Parr 1000 mL stainless steel bomb and heated at 165° C. for 3 hours. This produced a pressure of 200 psi. After cooling, the bomb contents were filtered and washed with cold ethanol to give a white solid. Successive concentrations and precipitations gave two additional batches of solid. Analysis of each solid by GC showed: crop 1, 66.1% (91% pure); crop 2, 12.9% (99% pure); crop 1, 5.9% (99% pure); total yield of bis-adduct was 79%. A repeat of this run, using a 1:2.5 ratio of BQ/isoprene and a reaction time of 2.5 hours, produced a semi-solid mixture which was suspended in 3 L of 50% aqueous ethanol. A solid was isolated by filtration and washed with 90% aqueous ethanol to afford, after drying, the bis-adduct (56%, 100% pure) as a white solid. The filtrate produced two more fractions by increasing the water ratio in the solution: crop 2, 8.4% (99% pure) and crop 3, 2.7% (86% pure); for a total yield of 67%.

Similar yields could be obtained at lower reaction temperatures and longer times. As an example, a run was performed in the Parr reactor at a 1:3 ratio of BQ/isoprene with slow heating from 24° C. to 104° C. (3.5 hr) and then 104° C. (5.5 hr). The internal pressure did not exceed 40 psi during the reaction. The semi-solid mixture was suspended in 3 L of 50% aqueous ethanol. A solid was isolated by filtration and washed with 90% aqueous ethanol to afford, after drying, the pure bis-adduct (66%) as a white solid (further crops were not collected in this case). In addition, a mixture of benzoquinone (2.50 g, 23.1 mmol) and isoprene (7.00 mL, 70.0 mmol, 3.0 equivalent) in ethanol (8.0 mL) was heated in a sealed vessel at 90–95° C. for 9 hours. The vessel was cooled and the contents removed. The resulting heterogeneous mixture was filtered and washed with methanol to afford 2.35 g of crude product. The filtrate was concentrated and the residue was crystallized from methanol/water to give an additional 1.32 g of product; thus, 3.67 g (15.0 mmol, 65%) of the bis-adduct was obtained as a white solid.

Analysis of the collected bis-adduct by GC/MS indicated the presence of three compounds, eluting very near one another, with identical molecular weights m/z: 244 ($M^+$). Several isomers are possible, based on the geometry of the methyl groups and the nature of the ring junctures relative to each other. The structures of the bis-adduct products were confirmed by $^1$H NMR (CDCl$_3$) δ5.37 (bs, 2H, =CH); 3.03 (apparent q, J=6 Hz, 2H, CHC=O); 2.96 (apparent q, J=6 Hz, 2H, CHC=O); 2.51–2.34 (m, 4H, CH$_2$—C=); 2.22–2.08 (m, 4H, CH$_2$—C=); 1.77 (bs, 6H, CH$_3$).

Oxidation of the Bis-Adduct to Give DMAQ

Attempts to oxidize the bis-adduct to DMAQ using basic hydrogen peroxide and chlorine dioxide failed; however, the bis-adduct was oxidized by two other methods. First, a suspension of the bis-adduct (10.5 mmol) in 100 mL of ethanol containing KOH (35.7 mmol, 3.40 equivalent) was heated at reflux under a stream of air. The mixture turned dark green and then dark red after heating for 1 h. After heating for an additional 3 h, the mixture was cooled, stirred at room temperature overnight, acidified to pH 1, and filtered. The collected crude product was purified by partitioning between ether and water. Evaporation of the ether solvent under reduced pressure gave DMAQ (8.52 mmol, 81%). A portion of this sample was further purified by recrystallization (EtOAc/hexane). Analysis by GC showed two components of nearly identical retention time; the synthesized DMAQ structure was confirmed by comparison of spectral properties to previously prepared DMAQ [Wozniak, J. C.; Dimmel, D. R.; and Malcolm, E. W. "Diels-Alder Reactions of Lignin-Derived Quinones," J. Wood Chem. Technol., 9, 513 (1989)]. A $^1$H NMR showed: (CDCl$_3$) δ8.19 (d, J=8 Hz, 2H, H-4+H-8 or H-5); 8.09 (d, J=1 Hz, 2H, H-1+H-5 or H-8); 7.58 (dd, J=1, 8 Hz, 2H, H-3+H-7 or H-6); 2.53 (s, 6H, ArCH$_3$). A mass spectrum displayed a strong molecular ion at m/e 236.

The oxidation was also accomplished by stirring the bis-adduct (32.8 mmol) in 95% ethanol (400 mL) containing KOH (321 mmol) in a Parr 1000 mL stainless steel bomb with a glass liner under an O$_2$ atmosphere (145 psi) at room temperature. As the bis-adduct was added to the colorless caustic solution, the color changed to dark green. When the reaction was completed (no longer a green or red color, 2 hr), a heterogeneous mixture was obtained which had a tan solid suspended in a clear solution. The mixture was diluted with water (400 mL) and acidified with concentrated HCl to pH 1. The mixture was filtered and the yellow/purple solid was suspended in 400 mL of methanol and filtered again. The solid was then dried under high vacuum and gave pure DMAQ (30.5 mmol, 93%). Attempts to carry out the same oxidation in water failed to give any reaction, presumably due to the insolubility of the adduct. Oxidations in 75% ethanol/water were slower—mixtures of DMAQ and bis-adducts were observed after two hours.

Pulping Results

The data in Table 1 presents a comparison of 1-kg pulping experiments with a southern pine and three catalysts: AQ, DMAQ, 2,6/7-dimethyloctahydroanthraquinone (bis-adduct). The cooks were done in duplicate; in the case of the soda/AQ, five cooks were performed. The reproducibly of the pulp characteristics in each case was quite good. The study specifically examined the resulting pulp yield, lignin content (kappa number), and fiber length (viscosity). A good pulping system provides a low kappa, high viscosity pulp. A control kraft cook with no catalyst gave kappa number of 37.5 (table entry 16). The kappa number for a corresponding soda control (not shown in the table) is expected to be about 60. So, catalyst addition to soda and kraft cooks provides a large benefit in lignin removal. Also, as expected, the addition of a catalyst to a kraft pulping system improved the pulp yield.

TABLE 1

Comparison of kappa numbers, yields, and viscosities from 1-kg pulping runs with pine.

| Cook Entry | Cook Type | Catalyst Type | % Cat. | Cook H-factor | Kappa No. Ave. | Screen Yield (%) | Vis-cosity |
|---|---|---|---|---|---|---|---|
| 1 | Soda | AQ | 0.100 | 2090 | 33.7 | 45.0 | |
| 2 | | | 0.100 | 2097 | 33.1 | 43.7 | |
| 3 | | | 0.100 | 2089 | 33.1 | 45.1 | |
| 4 | | | 0.100 | 2111 | 31.2 | 45.4 | |
| 5 | | | 0.100 | 2114 | 32.2 | 44.1 | 17.3 |
| 6 | | Bis- | 0.050 | 2124 | 33.6 | 45.6 | 18.2 |
| 7 | | Adduct | 0.050 | 2106 | 30.8 | 43.5 | 16.0 |
| 8 | | DMAQ | 0.050 | 2106 | 33.7 | 45.4 | 18.5 |
| 9 | | | 0.050 | 2108 | 35.2 | 45.6 | 18.1 |
| 10 | Kraft | AQ | 0.100 | 1214 | 30.3 | 46.8 | 36.7 |
| 11 | | | 0.100 | 1192 | 31.6 | 47.3 | 38.2 |
| 12 | | Bis- | 0.050 | 1195 | 31.8 | 46.1 | 40.2 |
| 13 | | Adduct | 0.050 | 1200 | 30.8 | 47.0 | 36.8 |
| 14 | | DMAQ | 0.050 | 1197 | 32.7 | 47.2 | 36.4 |
| 15 | | | 0.050 | 1197 | 31.3 | 46.5 | 37.7 |
| 16 | | none | | 1196 | 37.5 | 44.1 | 39.1 |

The data in Table 1 clearly show that the bis-adduct and DMAQ perform as well as AQ, at half the dose. The higher amount of NaOH and longer reaction times used in the soda cooks results in the expected lower viscosities, in comparison to the kraft cooks.

The bleachability of the catalysts pulps is an important parameter; bleachability relates the amount of bleaching chemicals consumed to reach a certain brightness. The pulps in Table 1 were bleached to full brightness (90 ISO) with a commercially practiced D(EOP)DED sequence [D=chlorine dioxide, E=extraction with NaOH, EOP=extraction with NaOH in the presence of oxygen and hydrogen peroxide]. The study established that there was no difference in brightness values versus chlorine dioxide consumed for the three soda/catalysts pulps. A similar observation was made for the kraft pulps, with and without catalyst. Thus, the bis-adduct and DMAQ catalysts-produced pulps that are as easy to bleach as AQ pulps.

Numerous modifications and variations in practice of the invention are expected to occur to those skilled in the art upon consideration of the foregoing detailed description of the invention. Consequently, such modifications and variations are intended to be included within the scope of the following claims.

What is claimed is:

1. A method for the delignification of lignocellulosic material, the method comprising:

delignifying lignocellulosic material with a pulping agent, and adding a dialkyl substituted octahydroanthraquinone to the lignocellulosic material in an amount effective to accelerate the delignification of the lignocellulosic material contained therein, wherein from about 0.01 weight % to about 0.50 weight % substituted octahydroanthraquinone is added to the lignocellulosic material to provide a pulping efficiency of at least about 10% higher than the pulping efficiency in a process without the additive.

2. A method as recited in claim 1 wherein the dialkyl substituted octahydroanthraquinone is substituted in the 2 and 7 positions or the 2 and 6 positions.

3. A method as recited in claim 1 wherein the octahydroanthraquinone is disubstituted with an alkyl group having one to eight carbon atoms.

4. A method as recited in claim 3 wherein the dialkyl substituted octahydroanthraquinone is substituted in the 2 and 7 positions or the 2 and 6 positions.

* * * * *